United States Patent
Säreläet al.

[11] Patent Number: 5,832,917
[45] Date of Patent: Nov. 10, 1998

[54] METHOD AND ARRANGEMENT FOR VAPORIZING AN ANAESTHETIC

[75] Inventors: Antti Särelä, Espoo, Finland; Erkki Heinonen, Järfälla, Sweden

[73] Assignee: Instrumentarium Oy, Helsinki, Finland

[21] Appl. No.: 589,218

[22] Filed: Jan. 22, 1996

[30] Foreign Application Priority Data

Jan. 23, 1995 [FI] Finland .................................. 950289

[51] Int. Cl.⁶ ................................................ A61M 16/01
[52] U.S. Cl. ................. 128/203.12; 128/203.16; 128/204.22; 128/203.26; 128/204.14
[58] Field of Search ........................ 128/203.12, 203.14, 128/203.25, 203.26, 203.27, 204.14, 204.18, 203.17, 203.16, 204.22

[56] References Cited

U.S. PATENT DOCUMENTS

| | | | |
|---|---|---|---|
| 3,251,361 | 5/1966 | Rusz | 128/202.22 |
| 3,703,172 | 11/1972 | Hay | 128/188 |
| 4,345,612 | 8/1982 | Koni et al. | 128/203.14 |
| 4,477,395 | 10/1984 | Albarda | 128/203.27 |
| 4,611,590 | 9/1986 | Ryschka et al. | 128/203.14 |
| 4,657,008 | 4/1987 | Broddner et al. | 128/203.27 |
| 4,770,168 | 9/1988 | Rusz et al. | 128/203.12 |
| 5,049,317 | 9/1991 | Kiske et al. | 128/203.14 |
| 5,146,915 | 9/1992 | Montgomery | 128/203.14 |
| 5,242,403 | 9/1993 | Falb et al. | 128/204.15 |
| 5,335,652 | 8/1994 | Falb et al. | 128/203.14 |
| 5,381,836 | 1/1995 | Braatz et al. | 128/200.21 |

FOREIGN PATENT DOCUMENTS

| | | | |
|---|---|---|---|
| 4105971 | 8/1992 | Germany | 128/203.25 |
| 2097272 | 11/1982 | United Kingdom | B01F 3/02 |

*Primary Examiner*—Vincent Milin
*Assistant Examiner*—V. Srivastava
*Attorney, Agent, or Firm*—Andrus, Sceales, Starke & Sawall

[57] ABSTRACT

A method and an arrangement in connection with vaporizing an anaesthetic, in which an anaesthetic, vaporized in a vaporizer is mixed with fresh gas and delivered to be inhaled by a patient. In order to achieve a reliable operation, the prevailing ambient air pressure is measured, the measured air pressure is compared with a reference pressure and when the prevailing ambient air pressure deviates from the reference pressure, the anaesthetic agent concentration of the fresh gas/anaesthetic mixture to be passed to the patient is adjusted in relation to the variation in the ambient external air pressure.

25 Claims, 1 Drawing Sheet

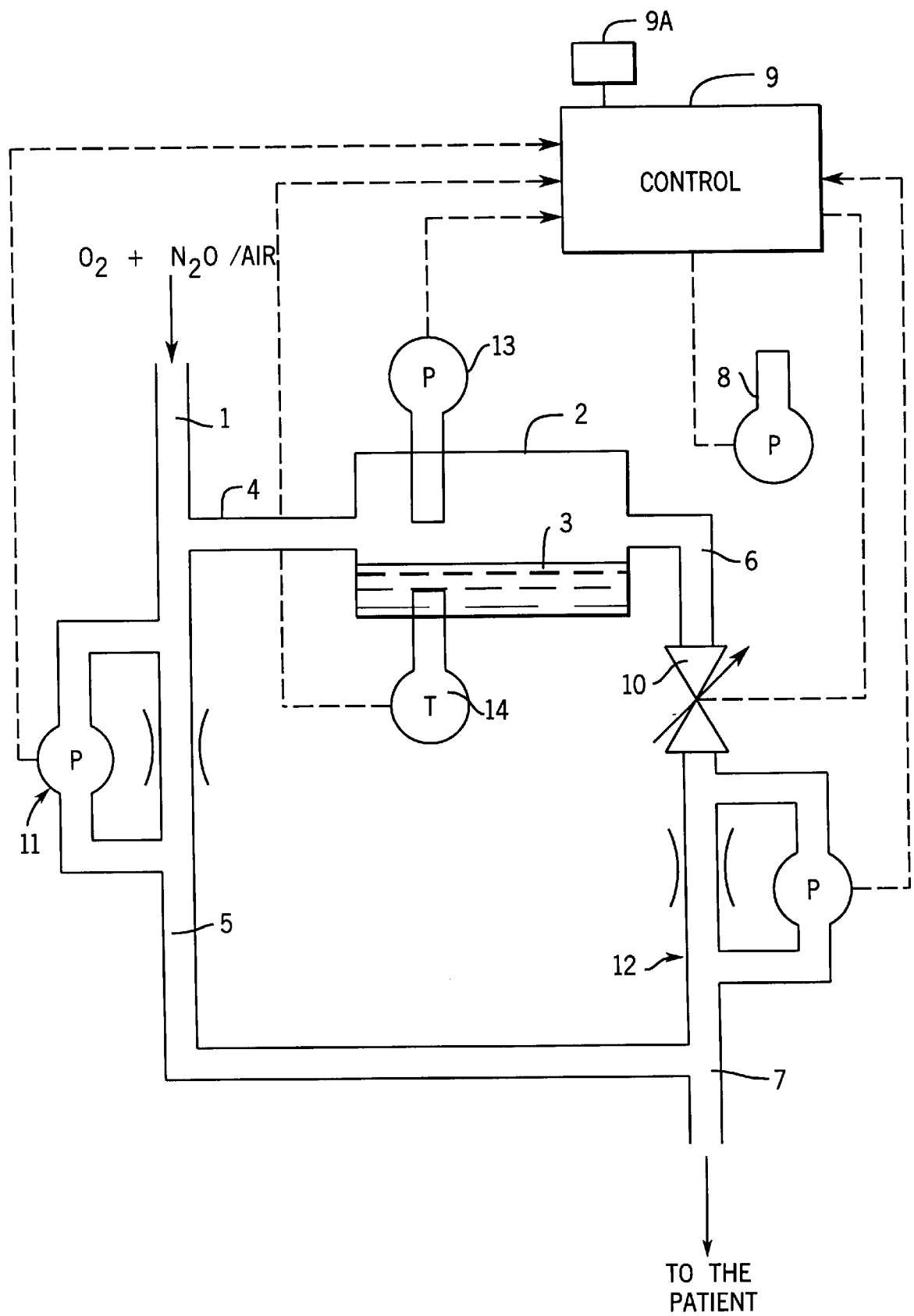

METHOD AND ARRANGEMENT FOR VAPORIZING AN ANAESTHETIC

BACKGROUND OF THE INVENTION

The present invention relates to a method for vaporizing an anaesthetic, in which an anaesthetic vaporized in a vaporizer is mixed with fresh gas and delivered to be inhaled by a patient. The invention also relates to an arrangement for vaporizing an anaesthetic.

An anaesthesia apparatus comprises an equipment in which a gas mixture is mixed of oxygen, air and nitrous oxide ($N_2O$, laughing gas) in a desired ratio and to which can be connected an equipment for vaporizing a liquid anaesthetic agent into said gas mixture. The connection of an anaesthetic vaporizer is often external, thus enabling vaporizers intended for vaporizing various anaesthetic agents to be connected to the system. An anaesthetic vaporizer can, however, be partly built-in in such a manner that only the liquid container specific for the anaesthetic liquid can be changed and the control equipment device in charge of dosing is built-in in the anaesthetic apparatus.

Anaesthetic agents in use at present include halothane, enflurane, isoflurane, cevoflurane and desflurane. Desflurane is different from other anaesthetic agents in that its boiling point is 23.5° C. while that of others varies both above and below 50° C.

Vaporizing techniques can generally be divided into the following types, that is, into by-pass, boilina and injection vaporizers.

The operation of vaporizers is most generally based on the principle of by-pass/dilution. All but desflurane of the anaesthetic agents mentioned above can be vaporized by means of this principle. In said principle, part of the fresh gas flow is passed via a container containing liquid anaesthetic and most of the fresh gas flow bypasses the container. The flow passing via the container is saturated with the vapour of the anaesthetic liquid into a concentration which is determined by the relation of the vapour pressure and the pressure prevalent in the container. conventional vaporizers, the pressure of the container is always close to the ambient air pressure.

The vapour pressure of the liquid is in practice independent of the variation in the ambient air pressure. Because of this, when the ambient air pressure decreases, the concentration provided by the vaporizer increases in relation to the relative decrease in the ambient air pressure.

The ambient air pressure mainly depends on the altitude above sea level, whereby the range of variation from the sea level to the altitude of 3500 m is from 1060 mbar to 630 mnbar, for example.

The depth of a patient's anaesthesia also depends on the amount of anaesthetic vapour, that is, on vapour pressure, instead of the relative concentration of the vapour. Therefore the higher relative concentration provided by the vaporizer in low air pressure compensates for the higher concentration required for a patient's anaesthesia in such a manner that the concentration of the anaesthetic agent selected for the vaporizer is independent of the ambient air pressure. In addition to the properties of the liquid, the vapour pressure of the liquid depends almost entirely on the temperature of the liquid. This has been utilized in a vaporizer arrangement based on cooling and heating that is disclosed e.g. in U.S. Pat. No. 3,251,361. In this method, the gas flow is passed in full via a vaporizer. The gas flow is saturated in the vaporizer, as is shown earlier, into a concentration determined by the relation of the vapour pressure and the pressure prevalent in the container that is close to the ambient air pressure. The required concentration is achieved by adjusting the temperature of the vaporizer either by cooling to heating so that the concentration of the anaesthetic vapour of the saturated gas flow will correspond to what is required. The principle of this arrangement can be applied to vaporize all the anaesthetic agents mentioned above.

A vaporizer based on the injection of an anaesthetic liquid is disclosed e.g. U.S. Pat. No. 4,477,395. In the equipment, the anaesthetic liquid is injected directly into the gas flow. The injected liquid is vaporized in full into the gas stream. The dosing is based on measuring the thermal energy bound by vaporizing the amount of liquid. U.S. Pat. No. 4,657,008 discloses a system in which dosing is controlled by measuring heat energy required for vaporization. This is performed by measuring the required electric power. An arrangement based on the dosing of liquid is disclosed in U.S. Pat. No. 5,242,403. In this arrangement, the liquid is administered by means of a motor-controlled pump, the amount to be pumped being based on the number of the revolutions of the pump. All these arrangements have in common the fact that the anaesthetic agent concentration of the produced gas mixture is independent of the ambient air pressure and as such it has to be taken into consideration in administering the anaesthesia. Furthermore, the arrangements can be applied to vaporize all the anaesthetic agents mentioned above.

Because of the low boiling point of desflurane, the use of this anaesthetic agent requires a vaporizing technique different from the conventional ones, and several arrangements based on injection are developed for vaporizing desflurane. In addition to these, desflurane vaporizers have been developed for operating either by cooling the liquid permanently below the boiling point or by heating it permanently above the boiling point. At the moment, there is only one vaporizer intended for this purpose on the market. Its operation is based on heating the anaesthetic agent to a temperature of +40° C. for example, which pressurizes the liquid container into a pressure of about 2 bar. From this pressure container, an anaesthetic vapour of 100% is mixed into the fresh gas flow so that the required anaesthetic concentration of the gas mixture will be attained.

On account of the operating principle of the desflurane vaporizer shown above, the concentration of the anaesthetic vapour from the liquid container is always 100% irrespective of the ambient air pressure. Therefore the anaesthetic agent concentration provided by the vaporizer is the same irrespective of the ambient air pressure. The depth of a patient's anaesthesia is determined also in this case by the amount of the anaesthetic vapour. Because of this, instructions are added to the directions for use of the vaporizer, for example, a diagram of the required adjustment correction of the vaporizer in thin atmosphere as compared with sea level. For example, at the altitude of 2,000 m the correction is about +25%.

In cooling desflurane vaporizers, the vaporization takes place exactly as in the above-described vaporizer operating on the by-pass principles.

The problem is that the cooling technique requires a lot of power and is slow to start when the liquid is warm.

SUMMARY OF THE INVENTION

The object of the invention is to provide an arrangement with which the drawbacks of the prior art can be eliminated. This has been achieved with the method and arrangement according to the invention. The method according to the invention is characterized in that the prevailing ambient air pressure is measured, the measured air pressure is compared with a reference pressure and when the prevailing ambient air pressure deviates from the reference pressure, the anaesthetic agent concentration of the fresh gas/anaesthetic mixture to be passed to the patient is adjusted in relation to the variation in the ambient air pressure The arrangement of the invention is characterized in that the arrangement comprises a sensor measuring the prevailing ambient air pressure and a control means arranged to compare the ambient air pressure with the reference pressure and when the ambient air pressure deviates from the reference pressure, to adjust by controlling the adjusting means the anaesthetic agent concentration of the mixture formed by vaporized anaesthetic and fresh gas to be passed to the patient in relation to the reference pressure and the air pressure data obtainable from the sensor measuring the ambient air pressure.

The primary advantage of the invention is that no separate correction tables or corrective measures are needed. In that case, the operation of a desflurane vaporizer is similar to the operation of a conventional vaporizer. A further advantage of the invention is that it can also be applied to vaporizers based on injection.

BRIEF DESCRIPTION OF THE DRAWINGS

In the following, the invention will be explained in more detail by means of one preferred embodiment illustrated in the accompanying drawing in which the only figure in the drawing shows a schematic diagrammatic view of the solution according to the invention.

DETAILED DESCRIPTION OF THE PREFERRED EMBODIMENT

The figure of the drawing illustrates a system utilizing the principle according to the invention.

In the figure, numeral 1 refers to a fresh gas line and numeral 2 to a vaporizer, The vaporizer 2 is naturally provided with means known per se for supplying an anaesthetic 3 to the vaporizer. Said means are not disclosed in the figure.

In the example of the figure, reference numeral 4 denotes a conduit along which part of the fresh gas flow is passed to the vaporizer 2. Reference numeral 5 denotes a by-pass conduit along which part of the fresh gas flow is passed by the vaporizer 2. Reference numeral 6 indicates an outlet conduit leading out of the vaporizer along which the mixture comprising fresh gas and anaesthetic vaporized in the vaporizer 2 is passed out of the vaporizer. Reference numeral 7 denotes a conduit along which the mixture flowing along the outlet conduit 6 and the by-pass conduit 5 is administered to the patient.

The operation and structure of the vaporizer represent fully conventional technology to those skilled in the art, and thus these procedures will not be explained in more detail in this context.

The essential idea of the invention is that the anaesthetic agent concentration of the fresh gas/anaesthetic mixture to be passed to the patient is adjusted in relation to the variation of the ambient air pressure. This adjustment is performed by means of a sensor 8 measuring the ambient air pressure and a control means 9. The measuring data of the sensor a is transmitted to the control means 9, as is shown by means of broken lines in the figure. The control means 9 is arranged to compare the measured air pressure with the reference pressure and to control a means 10 adjusting the anaesthetic agent concentration of the mixture comprising vaporized anaesthetic and fresh gas in relation to the reference pressure and the air pressure data obtainable from the sensor measuring the ambient air pressure. The reference pressure, which may be the air pressure of the sea level, for example, is separately supplied to the control means 9. The means 10 may be e.g. an adjustable valve with which the relation of the fresh gas flows passing via the conduits 4 and 5 is adjusted. Reference numeral 11 also indicated in the figure denotes a member measuring the flow of the by-pass conduit S and reference numeral 12 a member measuring the flow of the outlet conduit 6. Said members may be, for example, meters based on measuring the pressure difference or meters measuring the mass flow. The measuring data of the members 11 and 12 is transmitted to the control means 9, as is shown in the figure by means of broken lines. The concentration of the mixture being delivered to the patient can be monitored by means of said members. The monitoring of the concentration can also be accomplished otherwise, for example by means of a suitable analyzer, e.g. an infra-red analyzer. By arranging said analyzer to the conduit 7, for example, the member 12 will not be needed at all. In the figure, reference numeral 13 denotes a pressure sensor measuring the pressure prevalent inside the vaporizer 2 and reference numeral 14 a temperature sensor measuring the temperature of the anaesthetic liquid. The vapour pressure of the anaesthetic liquid is determined from the temperature measured by the temperature sensor 14, The overpressure with respect to the environment prevalent in the vaporizer is measured by the pressure sensor 13. The an aesthetic agent concentration of the gas flow to be passed to the conduit 6 is determined by the relation of the vapour pressure to the sum of the pressure prevalent in the vaporizer and the ambient pressure. The measuring data of these measuring devices is also transmitted to the control means 9, as is shown in the figure by means of broken lines. For example, an electronic unit can be used as the control means to which unit an interface 9a is connected for adjusting the required anaesthetic agent concentration.

The compensation of the anaesthetic agent concentration is performed by measuring the external air pressure by means of the sensor 8 measuring the air pressure, by comparing the measuring data with the reference pressure and by adjusting the dosing in relation no the measured air pressure and reference pressure. The concentration of the anaesthetic agent concentration will be increased when the external pressure decreases. For example, at the altitude of 2,000 m, the desflurane concentration is over-adjusted 25% with respect to the required concentration. In other respects, the arrangement operates in accordance with the selected operational principle.

The embodiment presented above is in no way intended to restrict the invention, but the invention may be modified fully freely within the scope of the claims. Therefore it is evident that the arrangement according to the invention or its details do not necessarily have to be identical to those shown in the figures but other solutions are possible as well. The invention is in no way restricted to be in connection with a desflurane vaporizer even if it is very suitable for this purpose, but the invention can also be employed in vaporizers based on injection, for instance. Although the invention i s above described by means of an arrangement in which part of the fresh gas flow is passed via the vaporizer and part of it bypasses the vaporizer, this is not the only possibility. It is also possible to employ this invention in arrangements in which fresh gas is not passed via the vaporizer.

We claim:

1. A method for mixing a vaporizable anaesthetic with fresh gas to form a breathing gas for a patient, said method controlling the concentration of anaesthetic in the breathing gas and comprising the steps of:

providing a flow stream of fresh gas;

supplying the anaesthetic to the fresh gas for mixing therewith to form a patient breathing gas containing vaporous anaesthetic;

controlling the supply of anaesthetic to the fresh gas to establish a concentration of anaesthetic in the breathing gas;

sensing ambient air pressure;

comparing ambient air pressure with a reference air pressure value; and altering the supply of anaesthetic to the fresh gas in accordance with said comparison to establish a desired concentration of anaesthetic in the breathing gas for the patient.

2. A method according to claim 1 wherein the step of altering the supply of anaesthetic is further defined as increasing the supply of anaesthetic when the ambient air pressure decreases with respect to the reference air pressure value.

3. A method according to claim 1 wherein the comparing step is further defined as comparing ambient air pressure with a reference air pressure value comprising air pressure at sea level.

4. A method according to claim 1 further defined as including the step of vaporizing a liquid anaesthetic to produce a vaporous anaesthetic and as mixing the vaporous anaesthetic so produced with the fresh gas to form the breathing gas.

5. A method according to claim 4 further defined as passing a portion of the fresh gas flow stream through a vaporizer containing the liquid anaesthetic to receive the vaporous anaesthetic and mixing the fresh gas flow stream portion containing the vaporous anaesthetic with the remaining portion of the fresh gas flow stream to form the breathing gas.

6. A method according to claim 5 wherein the altering step is further defined as controlling the flow of the fresh gas flow stream portion passed through the vaporizer.

7. A method according to claim 6 further including the step of measuring at least one of the temperature and pressure existing in the vaporizer and as controlling the flow of the fresh gas flow stream portion passed through the vaporizer responsive to said measurements.

8. A method according to claim 5 further defined as measuring gas flow in at least one of the fresh gas flow stream portion passed through the vaporizer and the remaining portion of the fresh gas flow stream.

9. A method according to claim 4 further defined as passing the fresh gas flow stream through a vaporizer containing the liquid anaesthetic to receive the vaporizer anaesthetic.

10. A method according to claim 1 further defined as a method for mixing desflurane with fresh gas.

11. A method according to claim 5 further defined as a method for mixing desflurane with fresh gas.

12. A method according to claim 1 wherein the anaesthetic supplying step is further defined as injecting vaporizable aesthetic into the fresh gas flow stream.

13. Apparatus for mixing an anaesthetic with fresh gas to form a breathing gas for a patient, said apparatus controlling the concentration of anaesthetic in the breathing gas and comprising:

conduit means couplable to a source of fresh gas for providing a flow stream of fresh gas;

means connected to said conduit means for supplying the anaesthetic to the fresh gas for mixing therewith to form a patient breathing gas containing vaporous anaesthetic;

means controlling the supply of anaesthetic to the fresh gas to establish a concentration of anaesthetic in the breathing gas;

means sensing ambient air pressure;

comparing means for comparing the ambient air pressure sensed by said sensing means with a reference air pressure value to determine the difference therebetween, said comparing means being coupled to said controlling means for causing said controlling means to alter the supply of anaesthetic to the fresh gas responsive to said air pressure difference for establishing a desired concentration of anaesthetic in the breathing gas for the patient.

14. An apparatus according to claim 13 wherein said comparing means is further defined as altering the supply of anaesthetic to increase the supply of anaesthetic to the fresh gas when the sensed ambient air pressure decreases with respect to the reference a pressure value.

15. An apparatus according to claim 13 wherein said comparing means is further defined as means for comparing ambient air pressure with a reference air pressure value comprising air pressure at sea level.

16. An apparatus according to claim 8 wherein said anaesthetic supplying means is further defined as means for vaporizing a liquid anaesthetic to produce vaporous anaesthetic and as mixing the vaporous anaesthetic with the fresh gas to form the breathing gas.

17. An apparatus according to claim 16 wherein said anaesthetic supplying means is further defined as bypass means for passing a portion of the fresh gas flow stream in said conduit means through a vaporizer containing the liquid anaesthetic to receive the vaporous anaesthetic and means for mixing the fresh gas flow stream portion containing the vaporous anaesthetic with the remaining portion of the fresh gas flow stream to form the breathing gas.

18. An apparatus according to claim 17 wherein said controlling means is further defined as located in said bypass means.

19. An apparatus according to claim 18 further including means for measuring at least one of the temperature and pressure existing in the vaporizer, said measuring means being coupled to said controlling means for controlling the flow through said bypass means responsive to the measurements of said measuring means.

20. An apparatus according to claim 17 further defined as including means for measuring gas flow in at least one of said bypass means and said conduit means.

21. An apparatus according to claim 16 wherein said anaesthesia supplying means further defined as means for passing the fresh gas flow through said vaporizer.

22. An apparatus according to claim 13 further defined as an apparatus for mixing desflurane with fresh gas.

23. An apparatus according to claim 17 further defined as an apparatus for mixing desflurane with fresh gas.

24. An apparatus according to claim 13 wherein said anaesthetic supplying means is further defined as means for injecting vaporizable anaesthetic into the fresh gas flow stream.

25. An arrangement according to claim 11, wherein the comprising means is an electronic unit.

* * * * *